US010617849B2

(12) United States Patent
Davies, Jr. et al.

(10) Patent No.: US 10,617,849 B2
(45) Date of Patent: *Apr. 14, 2020

(54) BALLOON WITH VARIABLE PITCH REINFORCING FIBERS

(71) Applicant: BARD PERIPHERAL VASCULAR, INC., Tempe, AZ (US)

(72) Inventors: William F. Davies, Jr., Athens, TX (US); Lanny R. Pepper, Larue, TX (US)

(73) Assignee: BARD PERIPHERAL VASCULAR, INC., Tempe, AZ (US)

( * ) Notice: Subject to any disclaimer, the term of this patent is extended or adjusted under 35 U.S.C. 154(b) by 356 days.

This patent is subject to a terminal disclaimer.

(21) Appl. No.: 14/954,456

(22) Filed: Nov. 30, 2015

(65) Prior Publication Data

US 2016/0082229 A1  Mar. 24, 2016

Related U.S. Application Data

(63) Continuation of application No. 12/890,092, filed on Sep. 24, 2010, now Pat. No. 9,211,391.

(60) Provisional application No. 61/245,453, filed on Sep. 24, 2009.

(51) Int. Cl.
*A61M 25/10* (2013.01)
*A61B 17/22* (2006.01)

(52) U.S. Cl.
CPC ...... *A61M 25/10* (2013.01); *A61B 2017/22001* (2013.01); *A61B 2017/22051* (2013.01); *A61M 25/104* (2013.01); *A61M 2025/1084* (2013.01)

(58) Field of Classification Search
CPC ........ A61M 25/104; A61M 2025/1084; A61M 25/10; A61M 25/1002; A61M 25/1027; A61M 2025/1031; A61M 2025/1059; A61M 2025/1075; A61M 2025/1081; A61M 2025/1086

See application file for complete search history.

(56) References Cited

U.S. PATENT DOCUMENTS

| 5,647,848 A * | 7/1997 | Jorgensen | A61M 25/104 604/103.11 |
| 6,626,861 B1 * | 9/2003 | Hart | A61B 17/22032 604/96.01 |

* cited by examiner

*Primary Examiner* — Katherine M Shi
*Assistant Examiner* — Lindsey Bachman
(74) *Attorney, Agent, or Firm* — King & Schickli, PLLC

(57) ABSTRACT

A medical balloon includes a generally cylindrical barrel wall having proximal and distal ends disposed between tapered cone walls and neck walls with a fiber layer comprised of circumferentially wrapped ribbon-shaped fiber embedded in a continuous matrix of polymer material defining the tapered cone walls and barrel wall, wherein the distance between the fiber wraps defines a fiber pitch or density that varies over the working length of the barrel wall in non-linear increments, for example in step-wise increments over the length of the barrel wall.

20 Claims, 10 Drawing Sheets

BALLOON WITH VARIABLE PITCH REINFORCING FIBERS

CROSS-REFERENCE TO RELATED APPLICATIONS

This application is a continuation of U.S. Pat. No. 9,211,391, filed on Sep. 24, 2010 and claims the benefit of U.S. Provisional Application No. 61/245,453, filed on Sep. 24, 2009.

TECHNICAL FIELD

The following disclosure relates to medical dilation balloons; and, in particular, it relates to non-compliant and semi-compliant medical balloons useful in angioplasty, stent placement and dilation and other medical applications including cardiology, radiology, urology and orthopedics.

BACKGROUND

Medical balloons are increasingly used in a wide variety of medical procedures. Typically, an uninflated medical balloon is inserted into a body-space, e.g., blood vessel, urological vessel, etc. by means of a catheter. After positioning at the desired location within the body, the medical balloon may be inflated by introducing a pressurized fluid into the balloon through the catheter. The pressurized fluid causes the medical balloon to expand, and the adjacent body-space is similarly expanded. The fluid may then be withdrawn from the balloon, causing it to collapse to facilitate its removal from the body. Medical balloons are also used for temporarily occluding vessels, placing medical devices such as stents, drug delivery and heat transfer.

Medical dilation balloons may be used to perform peripheral, for example, below-the knee, angioplasty to open a stenosis or occlusion of an artery, with or without stent placement. In some instances, this procedure requires that the balloon be threaded through small blood vessels along a tortuous path. Placement of the balloon may require that the balloon be forced through long calcified occlusions. Consequently, a number of characteristics are desired for medical dilation balloons used in these procedures.

In order to traverse a tortuous path to and/or through an occlusion, a high degree of trackability is desirable. In this context, the term "trackability" refers to the capability to traverse sharp turns or branches of the vessels or body cavities through which a balloon must pass. Balloons having more flexible walls generally provide better trackability. Since the balloon may be pushed through narrow and/or occluded blood vessels, a low profile (i.e., diameter) in the deflated state is also desirable. Further, a balloon should have good scratch resistance to avoid damage if it is pushed through a calcified occlusion.

Balloons used to place stents (an expandable metal sleeve), should have high puncture resistance, particularly at the areas of the balloon at the end of the stent. To avoid damaging the blood vessel's walls, the dilation balloon should exhibit low compliance. Balloon compliance is a term used to describe the change in a balloon's diameter as a function of pressure. Since the balloon may be used to open or expand tough tissues such as strictures, scarred or calcified areas, high pressures may be required. Thus, a balloon used in these applications should have high operating and burst pressures. The rated burst pressure is typically the maximum pressure at which there is a statistical 95% confidence level that 99.9% of the population of balloons will not burst. High-pressure non-compliant balloons may have rated burst pressures of up to 20 atmospheres or higher.

Generally, high pressure, non-compliant balloons are formed from relatively noncompliant (e.g. relatively inelastic) materials such as oriented highly crystalline polyethylene terephthalate (PET) films. Such PET films provide high tensile strength, and may be used to form balloons with thin walls having high burst pressures. However, balloons formed from PET and similar materials having a high strength relative to wall thickness tend to be susceptible to puncture and scratching.

Non-compliant medical balloons for performing angioplasty and other medical procedures are known. U.S. Pat. No. 6,746,425 to Beckham discloses a semi-compliant medical balloon and methods for manufacturing the balloon. U.S. Patent Application Publication No. US 2006/0085022 to Hayes et al. discloses a semi-compliant medical balloon having an integral woven fabric layer and methods for manufacturing the balloon. U.S. Patent Application Publication No. US 2006/0085023 to Davies, Jr. et al. discloses a medical balloon having strengthening rods and methods for manufacturing the balloon. U.S. Patent Application Publication No. US 2006/0085024 to Pepper et al. discloses a semi-compliant medical balloon having an integral non-woven fabric layer and methods for manufacturing the balloon. U.S. Pat. No. 6,746,425 and Publication Nos. US 2006/0085022, US 2006/0085023 and US 2006/0085024 are hereby incorporated herein by reference.

However, a need exists for improved medical dilation balloons having a low degree of compliance, thin walls, puncture resistance and improved trackability.

SUMMARY

In one aspect thereof, a fiber-reinforced medical balloon that may be inflated and deflated includes a generally cylindrical barrel wall having proximal and distal ends disposed between tapered cone walls and proximal and distal cylindrical neck walls extending from the cones along a longitudinal axis. The balloon includes a fiber layer embedded in a continuous matrix of polymer material defining a barrel wall, cone walls and neck walls wherein the barrel wall has a working length between the tapered cone walls. The fiber of the fiber layer extends circumferentially around the longitudinal axis of the balloon substantially over the entire length of the balloon including the neck walls, the cone walls and the barrel wall. The fiber pitch varies along the working length of the barrel portion with the fiber pitch in a first portion of the barrel wall being less than the fiber pitch in a second portion of the barrel wall. The working length of the balloon may vary from about four centimeters to about twenty-five centimeters, depending upon the specific application. In different embodiments, the balloon may be non-compliant or semi-compliant.

In one embodiment, the fiber pitch decreases from the proximal end of the barrel wall to the distal end of the barrel wall continuously or in a step-wise incremental manner. In another variation, the fiber pitch in first and second longitudinally spaced apart portions of the barrel wall is greater than the fiber pitch in a third portion of the barrel wall separating the spaced apart portions. In another embodiment, the fiber pitch in first and second longitudinally spaced apart portions of the barrel wall is less than the fiber pitch in a third portion of the barrel wall separating the first and second portions. In yet another variation, the fiber pitch in first, second and third longitudinally spaced apart portions of the barrel wall is greater than the fiber pitch in longitudinally spaced apart fourth and fifth portions of the barrel wall separating the first, second and third portions of the barrel wall.

In another embodiment, a medical balloon includes a generally cylindrical barrel wall having proximal and distal ends disposed between tapered cone walls. The balloon includes a fiber layer comprised of ribbon-shaped fiber embedded in a continuous matrix of polymer material defining tapered cone walls and a barrel wall disposed between the tapered cone walls. The fiber of the fiber layer extends around the longitudinal axis of the balloon in a series of circumferential fiber wraps with the distance between the fiber wraps defining a fiber pitch or density. In one aspect, the distance between adjacent fiber wraps varies over the working length of the barrel wall in non-linear increments, for example in step-wise increments over the length of the barrel wall.

In one aspect, the fibers of the fiber layer are ribbon-shaped, having a width-to-thickness ratio in the range from about 25:1 to about 45:1. In other variations, the fibers may have a width-to-thickness ratio in the range from about 30:1 to about 40:1. The medical balloon may also include distal cylindrical neck walls, the neck walls extending along a longitudinal axis of the balloon, extending from the cone walls along a longitudinal axis of the balloon with the fiber layer extending continuously between the ends of the neck walls around the cone sections and barrel wall. The flattened or ribbon-shaped fibers allow for thinner balloon walls while simultaneously reinforcing the balloon. The fibers may be formed from substantially inelastic or semi-elastic materials.

In yet another embodiment, an inflatable fiber-reinforced medical balloon includes a base balloon or base layer formed from a polymer material defining a barrel wall having a working length, cone walls extending from the barrel wall and neck walls extending from the cone walls along a longitudinal axis of the balloon. A fiber layer is disposed over the base balloon and extends over the working length of the barrel wall in a series of circumferential fiber wraps. The distance between adjacent circumferential wraps of the fiber defines a fiber pitch or density. An outer layer is formed from a polymer material is disposed over the fiber layer and adhered to the base balloon. The fiber pitch varies linearly or non-linearly over the working length of the balloon.

In another aspect, the walls of barrel portion and cone sections of the balloon form pleats or folds with creases between the folds. The folds or pleats extend longitudinally from proximal neck portions along the length of the cone and barrel portions of the balloon. In one embodiment at least three folds are formed in the walls of the cone and barrel portions of the balloon. In other variations, a greater or lesser number of folds and creases may be formed, for example two, four, six or ten folds may be formed. This pleated construction of the cone and barrel sections reduces the diameter of balloon to facilitate insertion of the balloon in its deflated state. Once positioned at the desired location, the balloon may be inflated through a catheter with a pressurized fluid such as a saline solution. As balloon is inflated, the folds and creases disappear as the balloon reaches a fully inflated size such that the outside surface of the balloon assumes a substantially smooth profile.

BRIEF DESCRIPTION OF THE DRAWINGS

For a more complete understanding, reference is now made to the following description taken in conjunction with the accompanying Drawings in which.

DETAILED DESCRIPTION

Figure 1A:
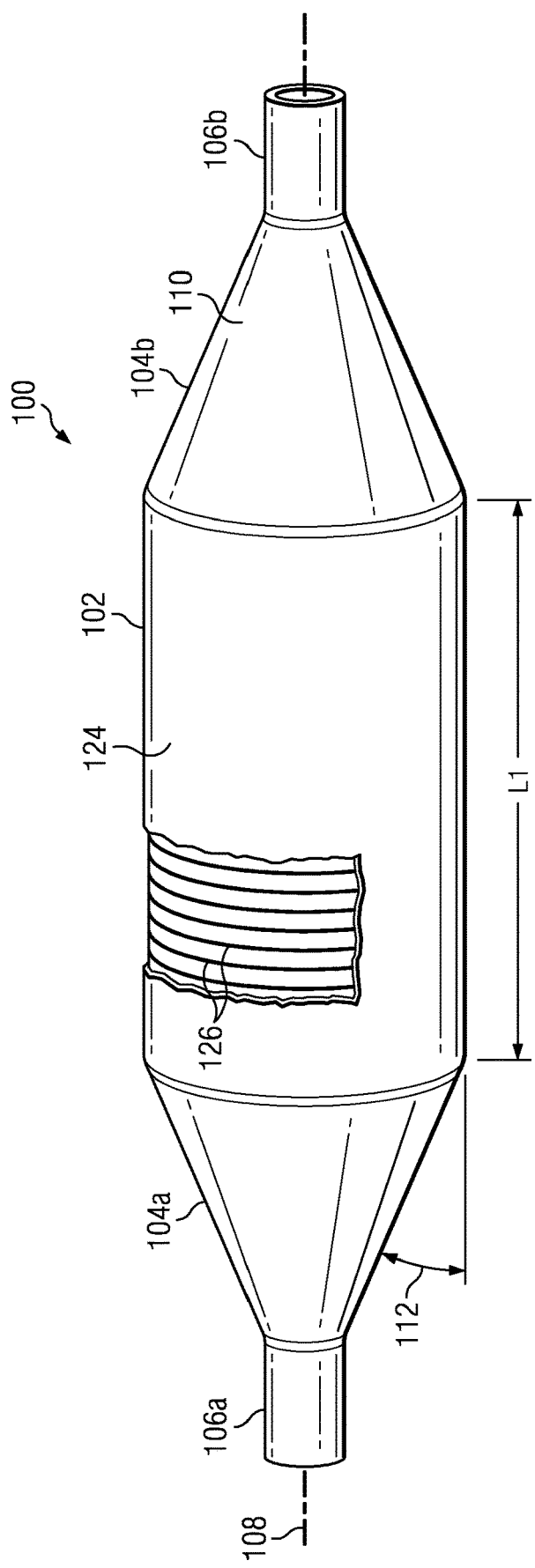
FIG. 1A is a partially cut away side view of a medical balloon with variable pitch fiber in an inflated state illustrating reinforcing fibers embedded in a wall of the balloon.

Referring now to the drawings, wherein like reference numbers are used herein to designate like elements throughout, the various views and embodiments of a balloon with variable pitch reinforcing fibers are illustrated and described, and other possible embodiments are described. The Figures are not necessarily drawn to scale, and in some instances the drawings have been exaggerated and/or simplified in places for illustrative purposes only. One of ordinary skill in the art will appreciate the many possible applications and variations based on the following examples of possible embodiments.

FIG. 1A is a side view of a fiber-reinforced semi-compliant medical dilation balloon according to one embodiment. As illustrated, medical balloon 100 is shown in a fully inflated state. Balloon 100 includes a generally cylindrical barrel portion 102 disposed between tapered proximal and distal cone portions 104a, 104b. A cylindrical proximal neck portion 106a and a cylindrical distal neck portion 106b extend from cone portions 104a, 104b along a longitudinal axis 108 of the balloon. The outer surface 110 of cone portions 104a, 104b each form an angle 112 (the "cone angle") with respect to a longitudinal extension of the wall of the barrel portion 102. In some embodiments, balloon 100 may have a cone angle 112 in the range of 12 degrees to 22 degrees, in others from 18 degrees to 22 degrees. Higher cone angles provide a shorter total balloon length and in some embodiments, the cone angle 112 is about 20 degrees. Balloon 100 may have a working length L1 between cone sections 104a, 104b of 4 to 25 cm or longer. In one embodiment, barrel portion 102 of balloon 100 comprises a generally cylindrical wall 124 with one continuous or a plurality of circumferential fibers 126 embedded in the wall.

In one embodiment, balloon 100 is non-compliant, i.e., it will expand typically less than about 5%, when pressurized from a nominal operating pressure to a rated burst pressure. In another embodiment, balloon 100 is semi-compliant, i.e. it will expand radially from about 5% to about 20% from its fully inflated diameter at a nominal operating pressure as the pressure of the fluid used to inflate the balloon increases to the balloon's rated burst pressure. While balloon 100 may be constructed to any dimensions, balloons having a deflated diameter in the range from about 2 French Units to about 12 French Units are useful in the fields of cardiology, radiology, orthopedics and urology. In one embodiment, balloon 100 has a deflated diameter in the range of 2 to 12 French Units and a folding wall thickness of less than about 0.002 inches.

Figure 1C:
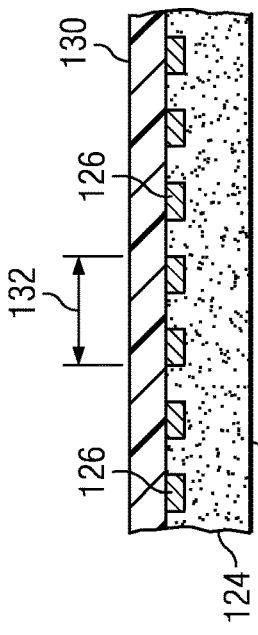
FIG. 1C is a partial longitudinal sectional view through the barrel wall of the balloon of FIG. 1A.
Figure 1B:
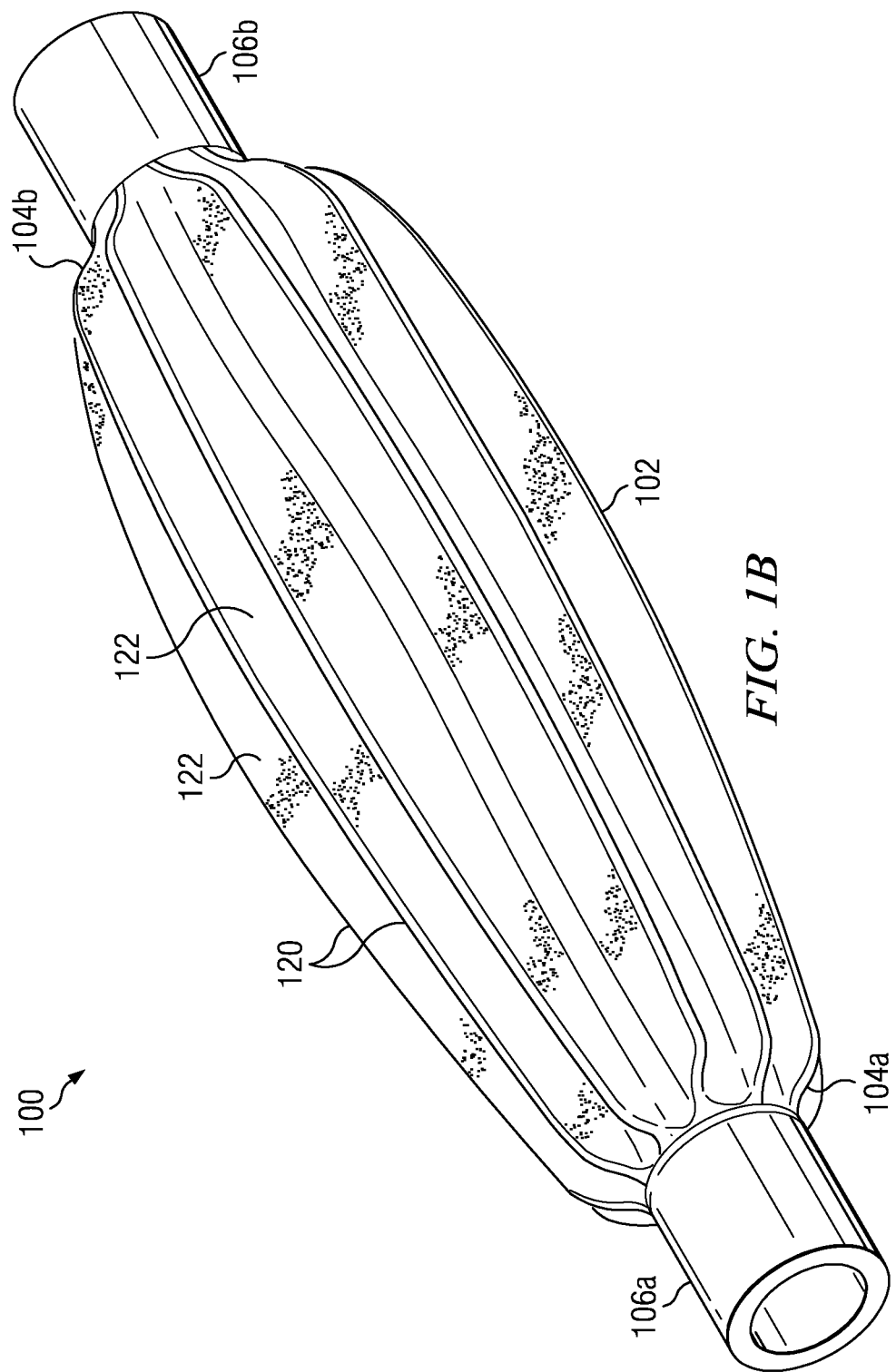
FIG. 1B is a perspective view of the balloon of FIG. 1 in a deflated state.

Referring to FIG. 1B, balloon 100 is illustrated in a deflated state. In its deflated state, the walls of barrel portion 102 and cone sections 104a, 104b of balloon 100 form pleats or folds 120 with creases 122 between the folds. As illustrated folds 120 extend longitudinally from proximal neck portion 106a to the opposing distal neck portion 106b. In one embodiment, at least three pleats or folds are formed, while in other embodiments, a greater or less number of folds or pleats may be formed to reduce the diameter of balloon 100 in its deflated state. The pleated construction of the cone and barrel sections, 104a, 104b and 102 reduces the diameter of balloon 100 to facilitate insertion of the balloon in its deflated state. Once positioned at the desired location, balloon 100 may be inflated through a catheter with a pressurized fluid such as a saline solution. As balloon 100 is inflated, folds and creases 120, 122 substantially disappear as the balloon reaches a fully inflated size.

FIG. 1C is a partial longitudinal section of barrel section 102 of balloon 100 according to one embodiment. As illustrated, barrel wall 124 includes one or more circumferential reinforcing fibers 126 embedded in a polymer layer 128 to form a fiber-reinforced wall structure. In one embodiment, a single fiber 126 extends from the proximal to the distal end of balloon 100 in a series of circumferential loops or wraps around the diameter of the balloon. As illustrated, fibers 126 are substantially ribbon-shaped in order to maintain the cross-sectional area and strength of the fiber while providing for a thinner wall 124. In different embodiments, fibers 126 may have a width-to-thickness ratio in the range from about 25:1 to about 45:1; in other variations, the fibers may have a width-to-thickness ratio in the range from about 30:1 to about 40:1.

Fibers 126 may be originally supplied in the form of a bundle or "tow" of individual filaments. The tow typically has a generally circular cross-section and may include an adhesive to hold the filaments together and retain the cross-sectional shape of the tow. Before use in constructing balloon 100, the tow is drawn between one or more pair of closely spaced rolls to flatten the tow. A solvent or solvent-based adhesive may be applied to the tow before it is drawn between the roll to soften any previously applied adhesive and to facilitate rearrangement of the filaments within the tow. After flattening, the fiber may be dried, if necessary, and used or stored for later use.

For non-compliant balloons, substantially inelastic reinforcing fibers 126 may be used. The reinforcing fibers 126 may be made from a variety of inelastic materials, including, but not limited to, Kevlar, Vectran, Spectra, Dacron, Dyneema, Turlon (PBT), Zylon (PBO), polyimide (PIM) and other ultrahigh molecular weight polyethylenes, aramids, and the like. In one embodiment, reinforcing fibers 126 may be multi-filament aramid or para-aramid fibers. In one variation, the fibers may be Technora® brand paraphenylene/3,4-oxydiphenylene/terephthalamide copolymer, preferably multi-filament. For semi-compliant balloons, reinforcing fibers 126 may be semi-elastic and have an elongation to break of from about 10% to about 20%. Reinforcing fibers 126 for a semi-compliant balloon may be formed from a nylon, such as nylon 6 or 6.6 or a high tenacity polyester.

Referring still to FIG. 1C, polymer base layer 128 may be formed from polymers and copolymers used in medical balloon construction, such as, but not limited to, polyethylene, polyethylene terephthalate (PET), polycaprolactam, polyesters, polyethers, polyamides, polyurethanes, polyimides, ABS copolymers, polyester/polyether block copolymers and ionomer resins. In one variation, barrel wall 124 may include an outer coating or layer 130, which may be the same as or similar to the polymer material in layer 128. In one variation, layers 128 and 130 may be formed from thermally-weldable materials such that the layers may be bonded or adhered together by heating. In other variations, a suitable adhesive such as a polyurethane may be used to bond layers 128 and 130. In still other embodiments, layers 128 and 130 may be bonded by solvent welding, ultrasonic, laser or infrared welding or other known methods.

The materials that form layer 128 and fibers 126 and outer layer 130 should be physically compatible. For example, if layer 128 is too soft, (e.g. too elastic, low tensile strength) relative to the material of fibers 126, the base balloon may extrude and/or blow out between fibers 126 at less than the desired operating pressure. Alternatively, if the material of layer 128 is too hard (e.g. too inelastic, high tensile strength) relative to fibers 126, balloon 100 may fail prematurely. Thus, the tensile properties (elasticity, tensile strength and elongation to break) of the materials used to form layer 128 and fibers 126 should be matched to prevent failure of the balloon while providing the desired burst pressure and level of compliance. For semi-compliant balloons, outer layer 130 should have suitable tensile properties (elasticity, tensile strength and elongation to break) sufficient to permit moderate expansion (5% to 20%) in a radial direction.

Referring still to FIG. 1C, the distance or "pitch" 132 between circumferential fibers 126 may vary over the length of the balloon 100. As used herein, the term "pitch" refers to the distance between fibers 126 measured from the center of one fiber to the center of an adjacent fiber along the longitudinal axis 108 of balloon 100. Thus, the "pitch" of fibers 126 may be expressed as the number of fibers per unit length, for example the number of fibers per inch. In one embodiment, balloon 100 includes a single fiber layer comprising variable pitch circumferential fiber or fibers 126. In other embodiments, balloon 100 may include additional fiber layers including longitudinally extending fibers, woven or non-woven fibers or knitted fibers. Balloon 100 may also include additional polymer layers.

Figure 2A:
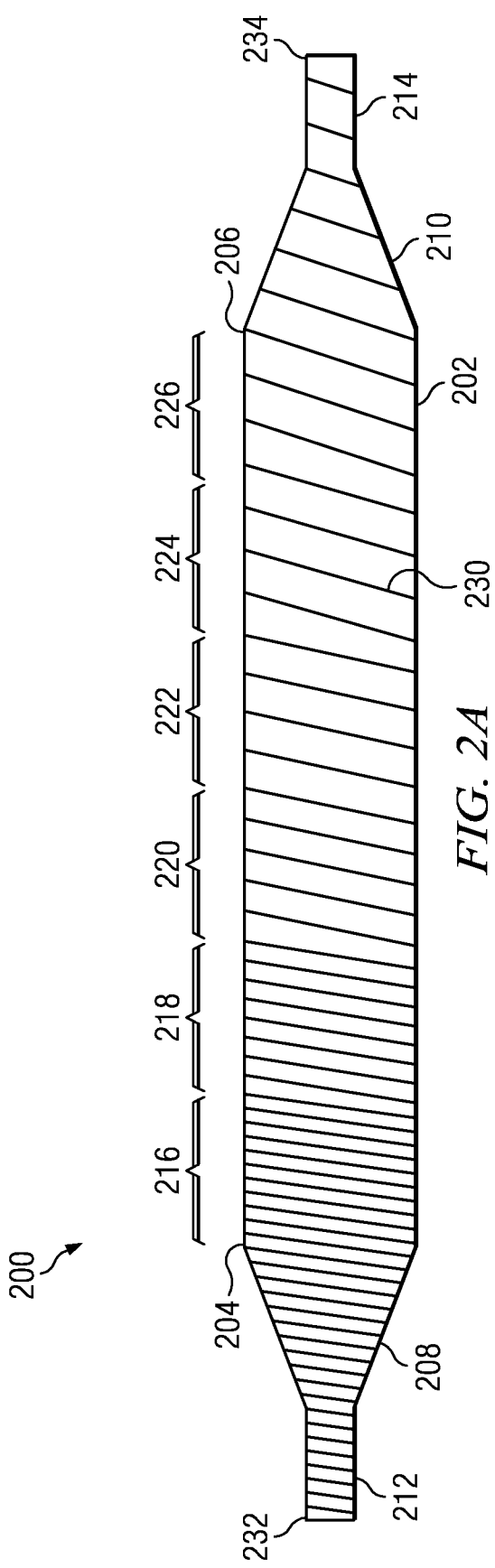
FIG. 2A illustrates the arrangement of reinforcing fibers in a first embodiment of a medical balloon according to the disclosure.

FIG. 2A is a side view of one embodiment of a medical balloon 200 illustrating the arrangement of one or more circumferential reinforcing fiber(s) 230 having an incrementally stepped variable fiber pitch along the length of the balloon. Balloon 200 has a generally cylindrical barrel portion 202 having a working length L2, a proximal end 204 and a distal end 206. Barrel portion 202 is disposed between a proximal cone portion 208 and a distal cone portion 210.

Proximal and distal neck portions 212, 214 extend longitudinally from proximal and distal cone portions 208 and 210. In one embodiment, the working length L2 of barrel portion 202 may be divided in a plurality of longitudinally extending zones 216, 218, 220, 222, 224 and 226, each of which has a different fiber pitch. In one embodiment, a single fiber 230 extends circumferentially around the diameter of balloon 200 from the proximal end 232 to the distal end 234 of balloon 200. In other embodiments, a plurality of fibers 230 may be used to reinforce balloon 200.

Figure 2B:
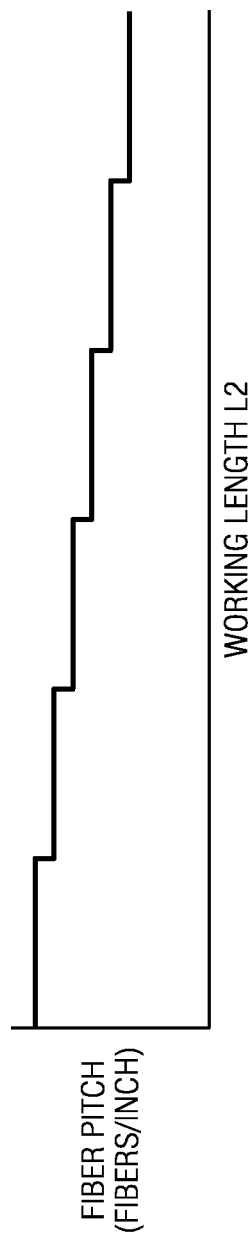
FIG. 2B is a graph representing the fiber pitch along the working length of the medical balloon of FIG. 2A.

FIG. 2B is a graph illustrating the fiber pitch in each of zones 216-226. As shown, the fiber pitch in zones 216-226 decreases in a step-wise fashion along the working length L2 of balloon 200 from the proximal end 204 of barrel portion 202 to the distal end 206 of the barrel portion. For example, the fiber pitch in zones 216-226 may be varied as followed:

| Zone: | 216 | 218 | 220 | 222 | 224 | 226 |
|---|---|---|---|---|---|---|
| Fiber Pitch: | 56 | 48 | 38 | 30 | 25 | 20 |

It will be appreciated that this example of the changes in the fiber pitch along barrel portion 202 of balloon 200 is only to illustrate one possible arrangement. The actual change in fiber pitch may vary due to a wide variety of factors including the size of balloon 200, the materials used to fabricate the balloon, the size of fibers 230, the material from which the fibers are made and the desired characteristics of the balloon. A greater or lesser number of zones having different fiber pitches may also be employed to achieve the desired characteristics.

In one embodiment, the fiber pitch in each of zones 216-226 remains the same within each zone, changing at the junctions between adjacent zones. Although as illustrated, the fiber pitch decreases in a step-wise fashion, other variations are possible. For example, there may be transition areas between zones 216-226 where the fiber pitch changes over segments of the working length L2 of barrel portion 202 in a linear or non-linear fashion.

Referring still to FIGS. 2A and 2B, decreasing the fiber pitch from the proximal end 204 of barrel portion 202 to the distal end 206 of the barrel portion reduces the stiffness of balloon 200 along the working length of the balloon. This, in turn, increases the trackability of the distal portion of balloon 200, increasing the balloon's capability to traverse sharp turns or branches of the blood vessels. Reducing the stiffness of the distal portion of balloon 200 may also decrease the risk of damaging a vessel wall. Alternatively, the more heavily reinforced proximal portion of balloon 200, wherein the closely spaced fibers 230 provide greater strength and puncture resistance, may be used to force open stenotic lesions.

In the illustrated embodiment, the fiber pitch in the proximal cone and neck portions 208, 212 of balloon 200 is substantially the same as the fiber pitch in the adjacent zones 216, 226 of barrel portion 202. Similarly, the fiber pitch in distal cone and neck portions 210, 214 of balloon 200 is the same or substantially the same as in the adjacent zones 216, 226 of barrel portion 202. In other embodiments, the fiber pitch in the cone portions 208, 210, and neck portions 212, 214 may be varied to improve the trackability or other characteristics of balloon 200.

Figure 3A:
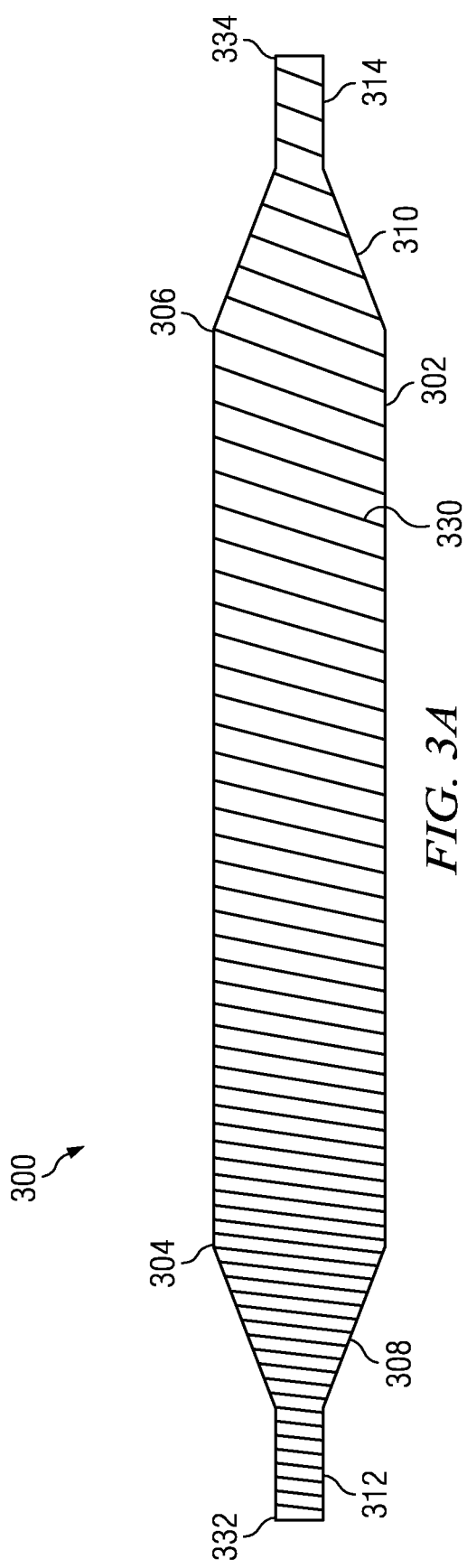
FIG. 3A illustrates the arrangement of reinforcing fibers in a second embodiment of a medical balloon according to the disclosure.

FIG. 3A is a side view of an embodiment of a medical balloon 300 having a continuously variable fiber pitch. Balloon 300 has a generally cylindrical barrel portion 302 having a working length L3, a proximal end 304 and a distal end 306. Barrel portion 302 is disposed between a proximal cone portion 308 and a distal cone portion 310. Proximal and distal neck portions 312, 314 extend longitudinally from proximal and distal cone portions 308 and 310. In the illustrated embodiment, one or more fibers 330 extend circumferentially around the diameter of balloon 300 from the proximal end 332 to the distal end 334 of balloon 300.

Figure 3B:
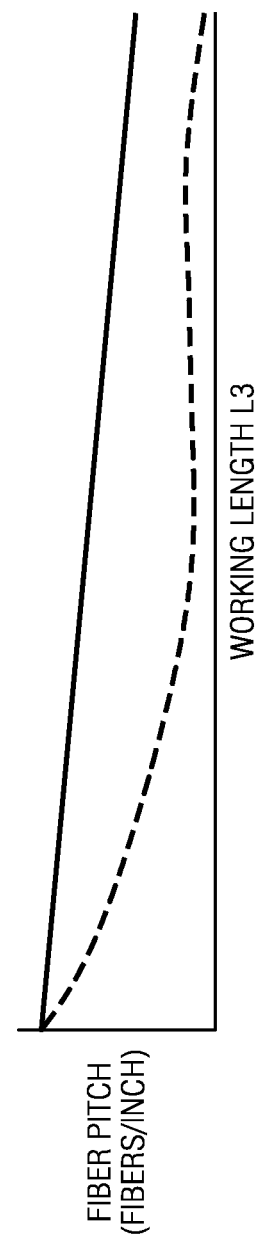
FIG. 3B is a graph representing the fiber pitch along the working length of the medical balloon of FIG. 3A.

FIG. 3B is a graph illustrating the change in fiber pitch over the working length of balloon 300. As illustrated, the fiber pitch decreases linearly from the proximal end 304 of barrel portion 302 to the distal end 306 of the barrel portion. For example, the fiber pitch may decrease linearly from about 60 fibers per inch at the proximal end 304 of barrel portion 302 to about 20 fibers per inch at the distal end 306 of the barrel portion. In other variations, the fiber pitch may decrease continuously in a non-linear manner from the proximal end 304 of barrel portion 302 to the distal end 306 of the barrel portion. For example, the fiber pitch may decrease along the curve represented by the dashed line in FIG. 3B. Decreasing the fiber pitch from the proximal end 304 of barrel portion 302 to the distal end 306 of the barrel portion reduces the stiffness of balloon 300 along the working length of the balloon, increasing the trackability of the distal portion of the balloon.

Stents are small, collapsible sleeves, typically formed from stainless steel and/or a suitable plastic that may be used in conjunction with angioplasty. For example, if a blood vessel does not remain open after angioplasty, a stent can be placed and expanded at the constricted location to hold the blood vessel open. The stent is typically placed over a deflated medical dilation balloon and positioned in the constriction. The balloon is then inflated one or more times to expand the stent in the blood vessel. After the stent has been positioned and expanded, the balloon is deflated and removed, leaving the expanded stent in the blood vessel. Often, high dilation pressures, for example 10-20 atmospheres are required to expand a stent. One concern in stent placement and dilation is the possibility of the balloon being punctured at the ends of the stent where the strain on the balloon is the greatest. If the balloon fails, during stent expansion, it may be caught on a partially expanded stent, possibly requiring surgical intervention.

Figure 4A:
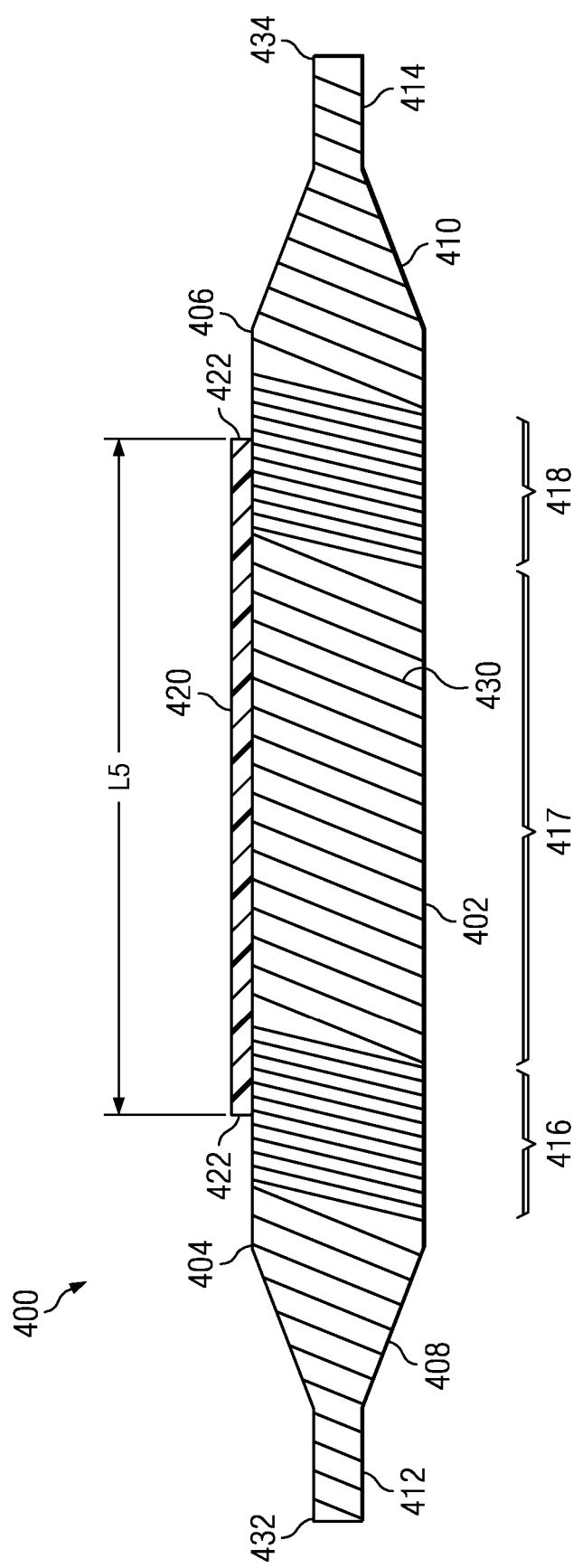
FIG. 4A illustrates the arrangement of reinforcing fibers in a third embodiment of a medical balloon according to the disclosure.

FIG. 4A is a side view of an embodiment of a medical balloon 400 having a step-wise variable fiber pitch with a higher pitch at selected locations along the balloon. As illustrated, balloon 400 includes a generally cylindrical barrel portion 402 having a working length L4, a proximal end 404 and a distal end 406. Barrel portion 402 is disposed between a proximal cone portion 408 and a distal cone portion 410. Proximal and distal neck portions 412, 414 extend longitudinally from proximal and distal cone portions 408 and 410. In the illustrated embodiment, one or more fibers 430 extend circumferentially around the diameter of balloon 400 from the proximal end 432 to the distal end 434 of balloon 400.

Figure 4B:
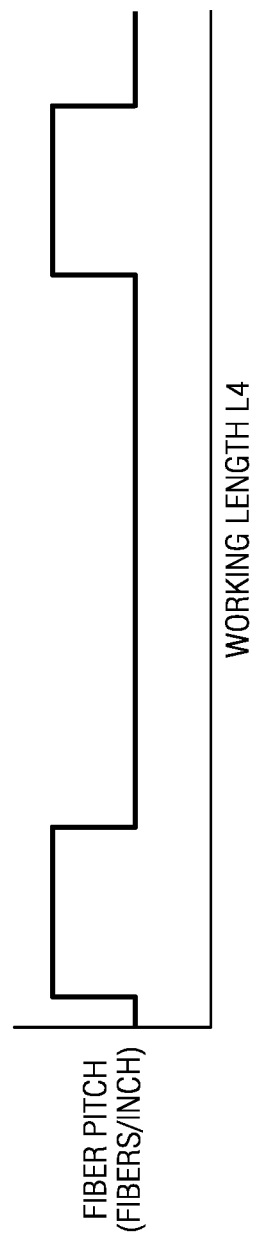
FIG. 4B is a graph representing the fiber pitch along the working length of the medical balloon of FIG. 4A.

FIG. 4B is graph illustrating the change in fiber pitch over the working length of balloon 400. As illustrated, barrel portion 402 includes a proximal zone 416 and a distal zone 418 having a higher fiber pitch than the remainder of the barrel portion. For example, zones 416 and 418 may have a fiber pitch of 60 wraps per inch of fiber 430 while the remainder of the balloon may have a fiber pitch of 30 wraps per inch. Zones 416 and 418 are separated by a central zone 417 having a lower fiber pitch with zones 416 and 418 spaced apart such that the ends 422 of a stent 420 having a length LS are positioned over highly reinforced zones 416 and 418 of barrel portion 402 of balloon 400. The increased fiber pitch in zones 416 and 418 serves to increase the strength and puncture resistance of balloon 400 at the ends of stent 420 during deployment and expansion of the stent.

Although as illustrated, zones 416, 418 are shown near or adjacent to the proximal and distal ends 404, 406 of barrel portion 402, the zones may be positioned in other locations along barrel portion 402 so long as the ends of a stent placed over the balloon are positioned over the highly reinforced zones. For example, it may be desirable to have distal zone 418 positioned further away from distal end 406 of barrel portion 402 to increase the flexibility and trackability of the distal portion of balloon 400. In the illustrated embodiment, the fiber pitch in proximal and distal cone and neck portions 408-414 is the same or substantially the same as the fiber pitch in the adjacent portions of barrel portion 402 (e.g. lower than that of reinforced zones 416, 418). In other embodiments, the fiber pitch in proximal and distal cone and neck portions 408-414 may be varied to improve characteristics of balloon 400 such as the trackability of the balloon.

Figure 5A:
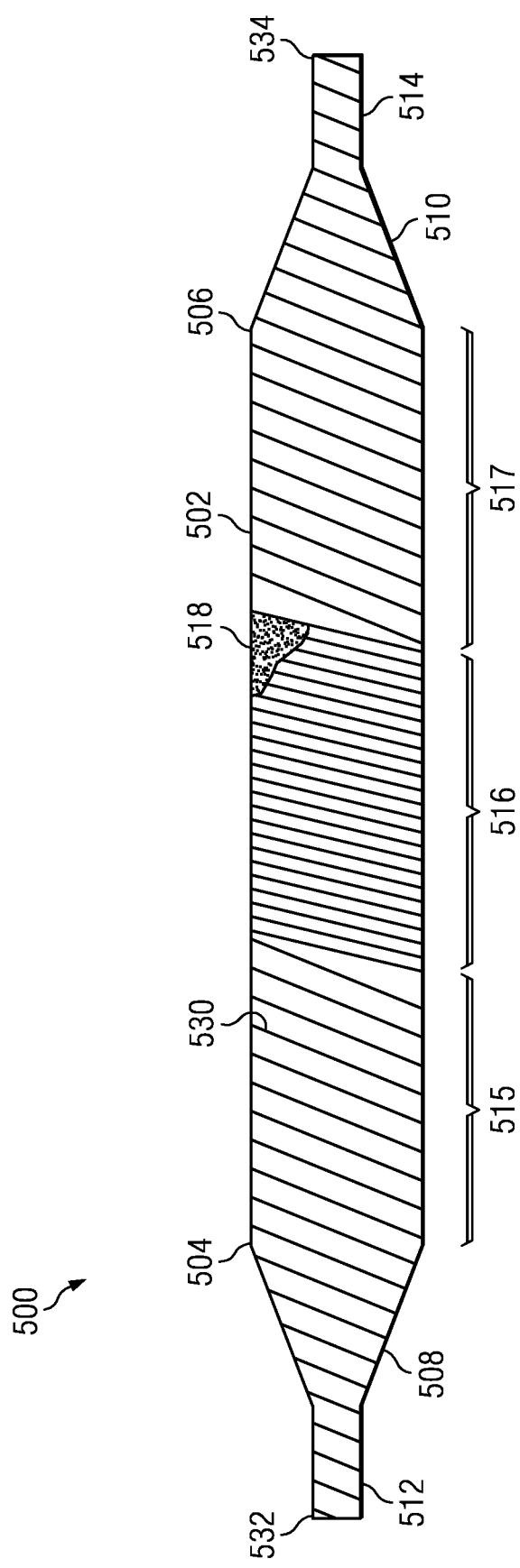
FIG. 5A illustrates the arrangement of reinforcing fibers in a fourth embodiment of a medical balloon according to the disclosure.

Medical dilation balloons may be used to break hard, calcified lesions in blood vessels. Such procedures may involve high dilation pressures and the concurrent risk that a sharp surface of the lesion may puncture or rupture the dilation balloon. FIG. 5A is a side view of an embodiment of a medical balloon 500 having a variable fiber pitch including a highly reinforced section. As illustrated, balloon 500 includes a generally cylindrical barrel portion 502 with a working length L5, a proximal end 504 and a distal end 506. Barrel portion 502 is disposed between a proximal cone portion 508 and a distal cone portion 510. Proximal and distal neck portions 512, 514 extend longitudinally from proximal and distal cone portions 508 and 510. In the illustrated embodiment, one or more fibers 530 extend circumferentially around the diameter of balloon 500 from the proximal end 532 to the distal end 534 of balloon 500.

Figure 5B:
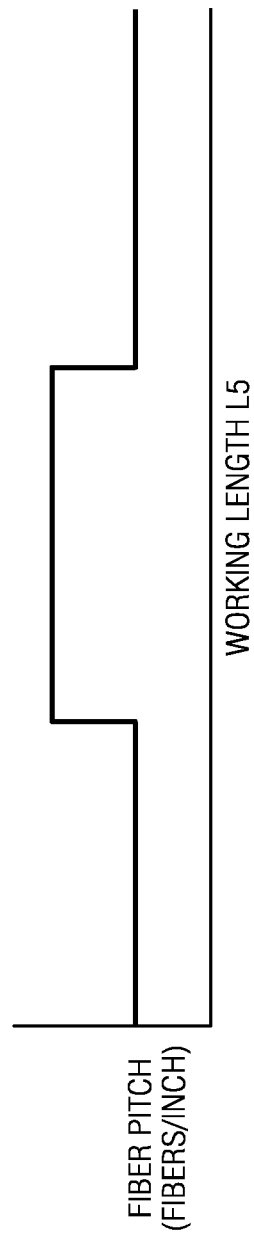
FIG. 5B is a graph representing the fiber pitch along the working length of the medical balloon of FIG. 5A.

FIG. 5B is a graph illustrating the change in fiber pitch over the working length of balloon 500. As illustrated, barrel portion 502 includes a proximal zone 515, a central zone 516 and a distal zone 517. As illustrated, zone 516 has a higher fiber pitch than the remainder of the barrel portion. For example, zone 516 may have a fiber pitch of 60 wraps of fiber 530 while proximal zone 515 and distal zone 517 may have a fiber pitch of 30 wraps per inch. Other fiber pitches are possible depending upon factors such as fiber size, the material from which fiber or fibers 530 are fabricated and desired wall thickness. The increased fiber pitch in zone 516 serves to increase the strength and puncture resistance of balloon 500 in the zone. The fiber pitch in cone portions 508, 510 and neck portions 512, 514 may be the same as or different from the fiber pitch in the adjacent proximal and distal barrel zones 515 and 517, respectively. In one embodiment, zone 516 may include a radio opaque marker 518 such as a radio-opaque coating. Radio-opaque marker 518 enables a practitioner using balloon 500 to position the balloon at the desired location in the blood vessel when performing angioplasty.

In some instances, a practitioner may use a dilation balloon to launch and/or deploy multiple stents at the same time. For example, if the available stents are not as long as the stenosis to be expanded, the practitioner may position two stents on a single dilation balloon with, for example, the proximal end of the distal stent overlapping the distal end of the proximal stent. However, overlapping stents in this fashion tends to create stress on the dilation balloon in the overlapped area when the balloon is inflated to expand the stents.

Figure 6A:
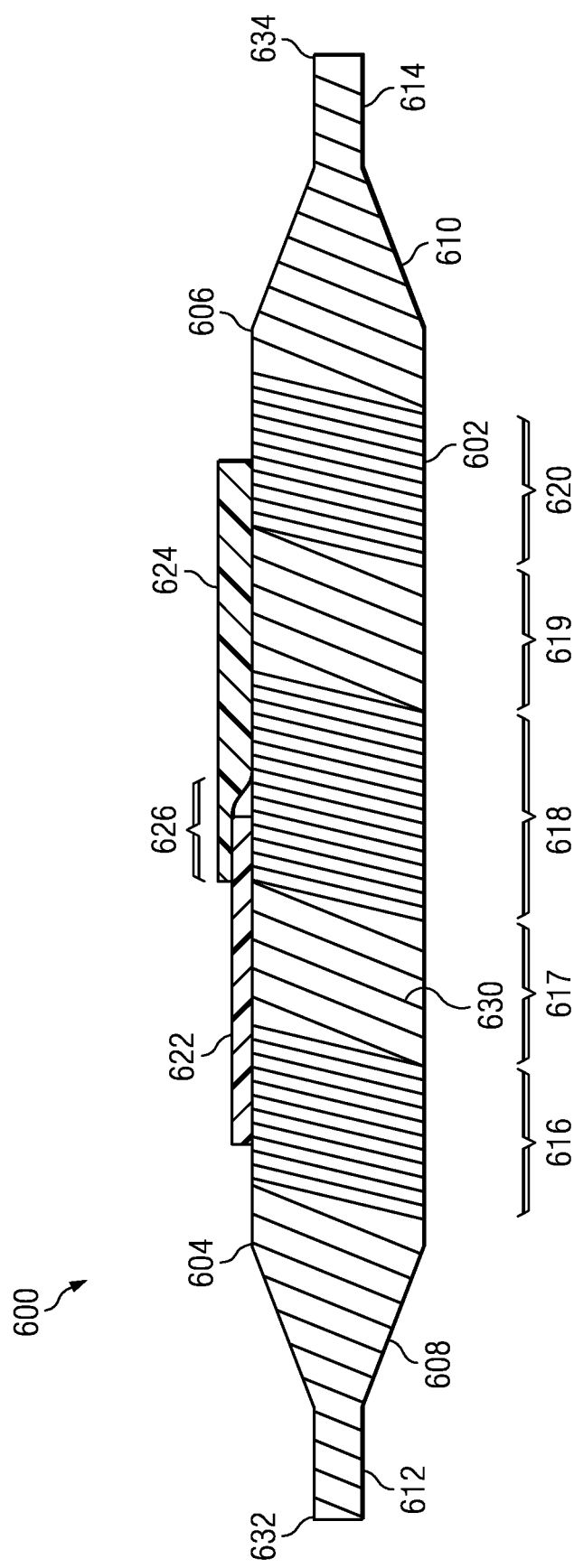
FIG. 6A illustrates the arrangement of reinforcing fibers in a fifth embodiment of a medical balloon according to the disclosure.

Referring now to FIG. 6A, in one embodiment, a medical dilation balloon 600 having variable pitch reinforcing fibers adapted to launch multiple stents having overlapping ends includes multiple highly reinforced areas. In one embodiment, balloon 600 includes a generally cylindrical barrel portion 602 with a working length L6, a proximal end 604 and a distal end 606. Barrel portion 602 is disposed between a proximal cone portion 608 and a distal cone portion 610. Proximal and distal neck portions 612, 614 extend longitudinally from proximal and distal cone portions 608 and 610. In the illustrated embodiment, one or more fibers 630 extend circumferentially around the diameter of balloon 600 from the proximal end 632 to the distal end 634 of balloon 600.

Figure 6B:
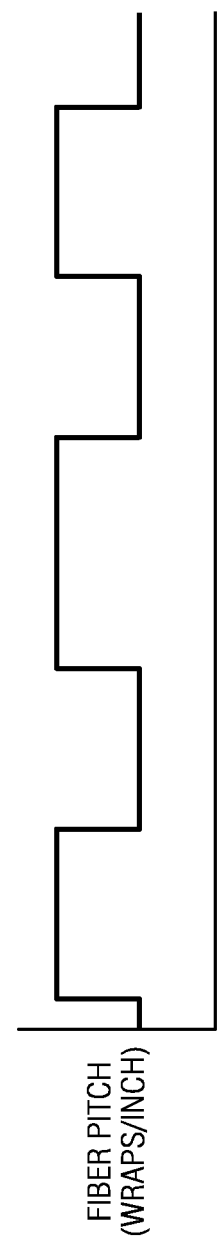
FIG. 6B is a graph representing the fiber pitch along the working length of the medical balloon of FIG. 6A.

FIG. 6B is graph illustrating the change in fiber pitch over the working length of balloon 600. As illustrated, barrel portion 602 includes longitudinally spaced apart proximal, intermediate and distal zones 616, 618 and 620 having a higher fiber pitch than the remainder of the barrel portion. In one variation, zones 616, 618 and 620 are separated by longitudinally spaced apart zones 617 and 619 which have a lower fiber pitch. For example, zones 616, 618 and 620 may have a fiber pitch of 60 wraps of fiber 630 while the remainder of the balloon, including zones 617 and 619, may have a fiber pitch of 30 wraps per inch. In other variations, the fiber pitch in intermediate zone 618 may be greater than the fiber pitch in proximal and distal zones 616, 620 which in turn, may be higher than in other portions of balloon 600. Other fiber pitches in the different zones are possible. As illustrated, zones 616 and 620 are spaced apart such that a proximal end of proximal stent 622 may be placed over zone 616 and the distal end of a distal stent 624 may be placed over zone 620. The overlapping end portions 626 of stents 622 and 624 are positioned over intermediate zone 618. The increased fiber pitch in zones 616 and 620 serves to increase the strength and puncture resistance of balloon 600 at the proximal end of proximal stent 622 and at the distal end of distal stent 624. The increased fiber pitch in intermediate zone 618 increases the strength and puncture resistance in the area of the overlapping stent ends.

As illustrated, proximal and distal zones 616, 620 are shown near or adjacent to the proximal and distal ends 604 and 606 of barrel portion 602 with intermediate zone 618 centrally located between the proximal and distal zones. In other variations, zones 616, 618 and 620 may be positioned in other locations along the barrel portion so long as the ends and overlapping portions of stents 622 and 624 are positioned over the highly reinforced zones. For example, if stents 622 and 624 have different lengths, intermediate zone 618 may be closer to the proximal end 604 or distal end 606 of barrel portion 602. It may also be desirable to have distal zone 620 positioned further away from distal end 606 of barrel portion 602 to increase the flexibility and trackability of the distal portion of balloon 600. In one embodiment, the fiber pitch in proximal and distal cone and neck portions 608-614 is the same or substantially the same as the fiber pitch in the adjacent portions of barrel portion 602 (e.g. lower than that of reinforced zones 616, 618 and 620). In other embodiments, the fiber pitch in proximal and distal cone and neck portions 608-614 may be varied to improve characteristics of balloon 600 such as the strength and trackability of the balloon.

Figure 7:
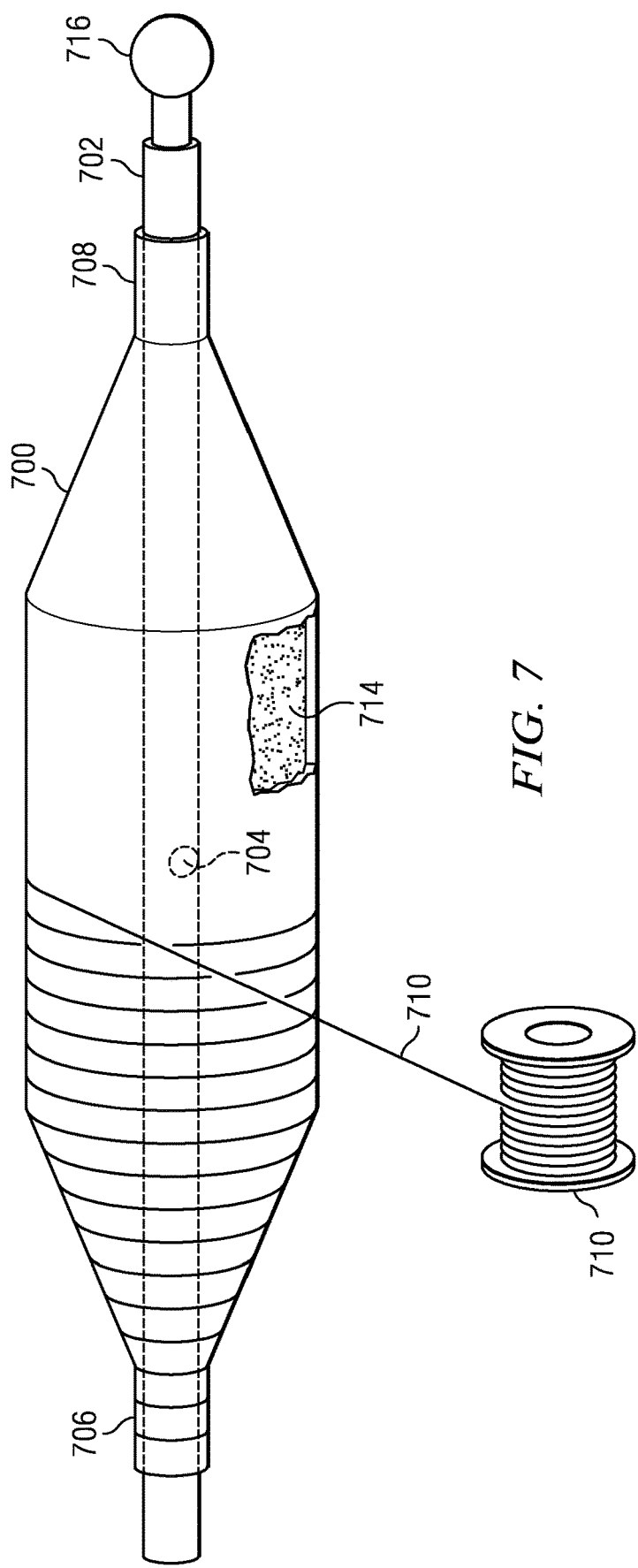
FIG. 7 illustrates the placement of reinforcing fibers on a base balloon.

Turning now to FIG. 7, in one embodiment, a method of fabricating a balloon having variable pitch reinforcing fibers begins with the formation of a base balloon 700. Base balloon 700 corresponds to polymer layer 128 of FIG. 1C and may be formed with conventional blow molding techniques or by coating a removable mandrel having the desired final shape of the balloon with one or more layers of a polymer solution, curing the solution and removing the mandrel. In other variations, base balloon 700 may be formed from other materials such as a polyethylene, nylon or a polyether block amide (PEBA). A hollow tube-shaped mandrel 702 having a side opening 704 is inserted through the balloon and the neck portions 706, 708 of base balloon 700 are sealed against the mandrel. A source of pressurized air 716 is connected to mandrel 702 and base balloon 700 is pressurized through opening 704.

Referring still to FIG. 7, with base balloon 700 pressurized, one or more flattened reinforcing hoop fibers 710 are wound circumferentially around the base balloon. In one embodiment, a single reinforcing hoop fiber 710 is wound circumferentially from the proximal end of proximal neck portion 706 to the distal end of distal neck portion 708. Flattened fibers 710 may be supplied from a storage drum or spool 712. The circumferential winding of fiber 710 may be accomplished by revolving spool 712 around mandrel 702 and balloon 700 while indexing the mandrel and balloon past the spool. In other embodiments, mandrel 702 and balloon 700 may be rotated as spool 712 is indexed along the length of base balloon 700. In any case, the pitch at which fiber 710 is applied to base balloon 700 may be controlled by varying the linear speed at which mandrel 702 and balloon 700 are indexed past spool 712 or vice versa. Alternatively, the pitch may be varied by controlling the rate at which fiber 710 is wound onto the balloon while indexing the mandrel 702 and balloon 700 (or spool 712) at a constant linear speed. In either case, the fiber of the fiber layer extends around the longitudinal axis of the balloon in a series of circumferential fiber wraps over the length of the barrel wall with the distance between adjacent fiber wraps varying according to linear speed at which mandrel 702 and balloon 700 are indexed past spool 712 or vice versa. The distance between the fiber wraps may be varied in a stepwise fashion or in a linear increasing or decreasing manner.

Prior to winding the hoop reinforcing fibers 710 onto base balloon 700, an adhesive coating 714 may be applied to the surface of balloon 700 to aid in retaining the fibers at the desired location. The coating 714 may be applied by spraying, brushing or dipping and may be selectively applied to different portions of balloon 700. For example, the adhesive may be applied only to the cone portions of balloon 700 since the tendency for hoop fibers 710 to slip is greatest on the angled surfaces of the cones. Alternatively, an adhesive may be applied to fiber or fibers 710 before the fibers are wound onto the base balloon.

After fibers 710 have been wound onto base balloon 700, an adhesive, such as a polyurethane, may be applied to the outer surface of the fiber-wrapped balloon to facilitate attachment of an outer layer to the balloon. In one embodiment, a thermally-weldable polymer solution such as a soluble nylon coating may be applied to facilitate thermal bonding in a later processing step. The adhesive and/or polymer solution may be applied by spraying, brushing or dipping and may be selectively applied to different portions of balloon 700.

Figure 8:
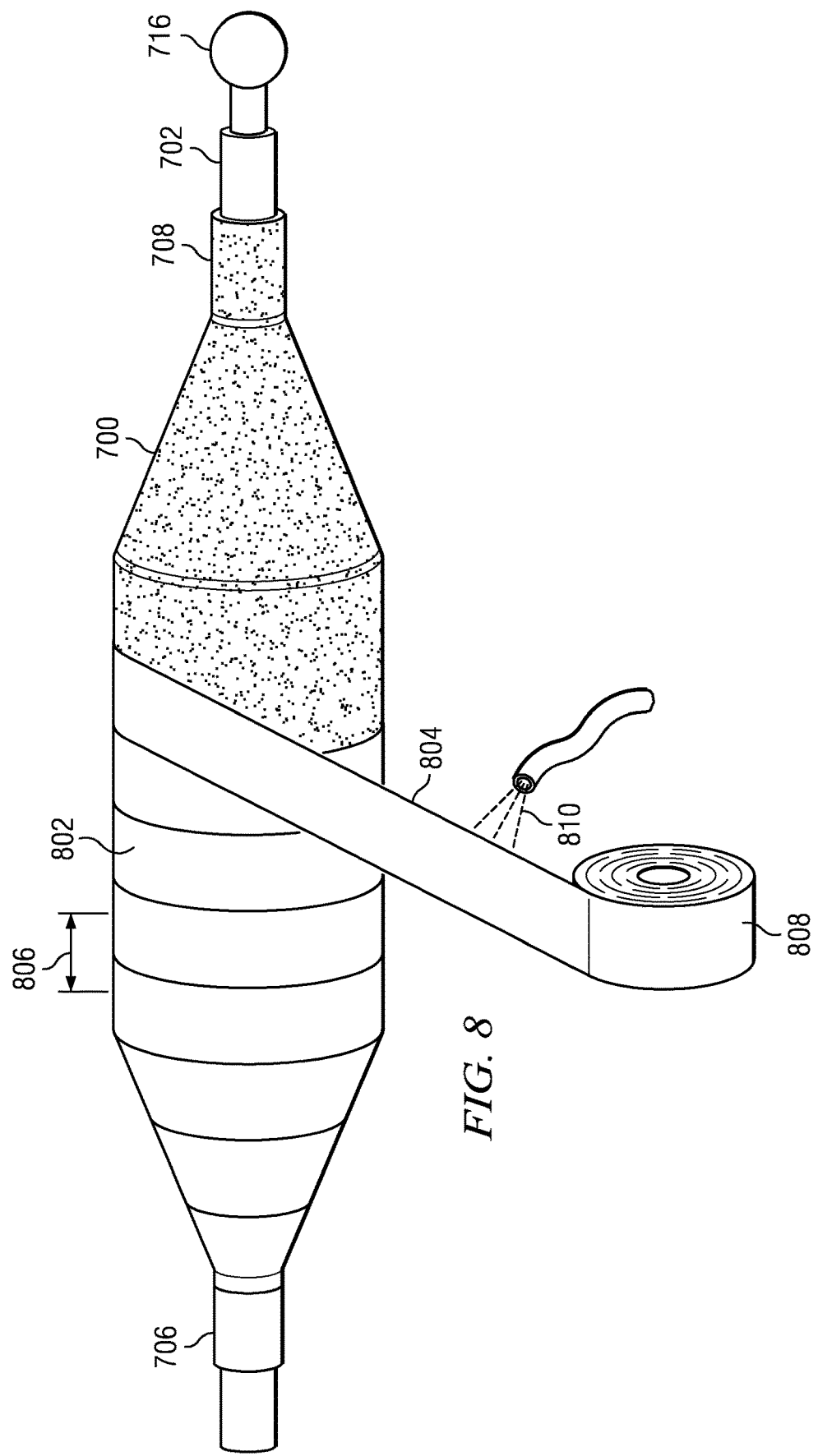
FIG. 8 illustrates the application of an outer cover layer over the fiber wrapped balloon of FIG. 7.

Referring now to FIG. 8, in one embodiment, an outer layer 802 is formed over fibers 710. In one embodiment, outer layer 802 may be a polymer tape or film 804 wrapped circumferentially around the balloon 700 at a predetermined pitch 806. Pitch 806 may be selected to be smaller than the width of polymer tape 804 so that successive winds of the tape will overlap, insuring complete coverage of base balloon 700. Tape 804 may be supplied from a storage drum 808. The circumferential winding of tape 804 onto balloon 700 may be accomplished by revolving drum 808 around mandrel 702 and balloon 700 while indexing the mandrel and balloon past the drum. In other embodiments, mandrel 702 and balloon 700 may be rotated while drum 808 is indexed along the length of balloon 700.

In one embodiment, tape 804 is wound continuously around balloon 700 from the proximal end of proximal neck portion 706 to the distal end of distal neck portion 708 of balloon 700 to form a continuous outer layer 802 over the entire balloon. Tape 804 may be formed from the same material as base balloon 700 or a different material. In one variation, outer layer 802 may be formed from a PEBA, (e.g., Pebax®) tape or film, stretched to a thickness of about 0.0003 inches. In one variation, the side of tape 804 to be applied to base balloon 700 may be coated with an adhesive 810, such as a polyurethane, to facilitate placement of the tape on base balloon 700. Adhesive 810 may be applied to tape 804 by spraying, brushing, dipping or other means.

Figure 9:
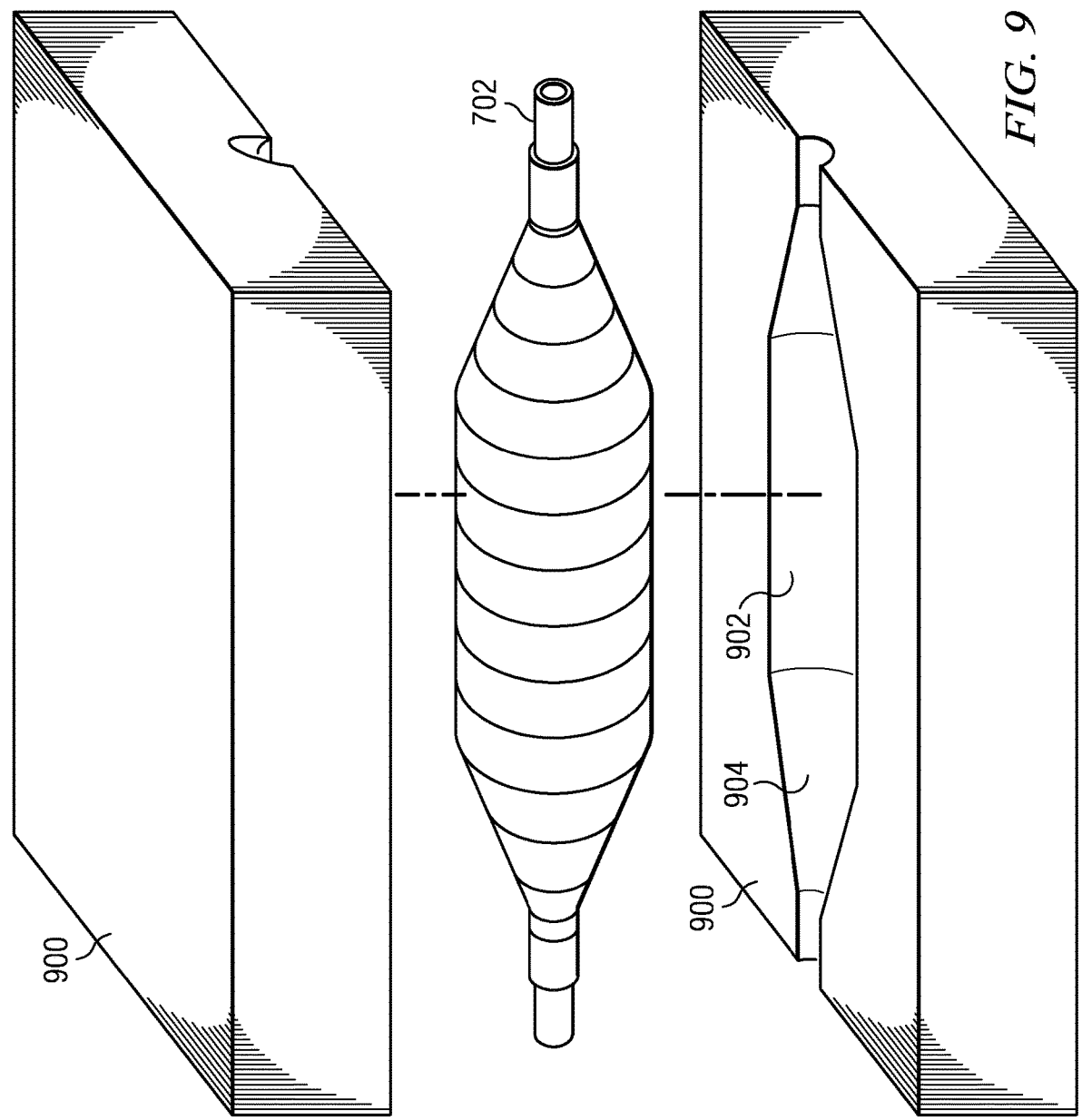
FIG. 9 illustrates the placement of the balloon of FIG. 8 in a die for heating and finishing of the balloon.

Turning to FIG. 9, after outer coating 802 has been applied to base balloon 700 over fibers 710, the balloon, still mounted on mandrel 702 is placed into a die 900 having a balloon-shaped cavity 902 and heated. Balloon 700 may be pressurized through mandrel 702 to conform the walls of the balloon to the inner walls 904 of the die during the heating process. In one embodiment, die 900 may be placed in an oven during the heating process. In another variation, die 900 may include internal heating elements.

During the heating process, base balloon 700 and/or outer coating 802 may soften sufficiently to encapsulate fibers 710 in a continuous polymer matrix as illustrated in FIG. 1C. If base balloon 700 and outer coating 802 are thermally-weldable materials, the two layers may fuse together during the process. In some embodiments, outer layer 802 may plastically deform under heat and pressure to even out any surface irregularities, for example locations where tape 804 has been overlapped such that the outer surface of the finished balloon is continuous and smooth.

It will be appreciated by those skilled in the art having the benefit of this disclosure that a medical balloon with variable pitch reinforcing fibers balloon may provide improved flexibility and trackability with increased strength and puncture resistance in selected areas of the balloon. It should be understood that the drawings and detailed description herein are to be regarded in an illustrative rather than a restrictive manner, and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

What is claimed is:

1. A fiber-reinforced medical balloon that may be inflated and deflated, the balloon comprising:
    a fiber layer embedded in a continuous matrix of polymer material defining a generally cylindrical barrel wall in an inflated condition;
    wherein the fiber of the fiber layer extends circumferentially around a longitudinal axis of the balloon over at least a portion of said barrel wall; and
    wherein the fiber pitch in a first portion of the barrel wall is less than the fiber pitch in a second portion of the barrel wall.

2. The fiber-reinforced medical balloon of claim 1 wherein the fiber pitch decreases from a proximal portion of the barrel wall to a distal portion of the barrel wall.

3. The fiber-reinforced medical balloon of claim 1 wherein the fiber pitch decreases from a proximal portion of the barrel wall to a distal portion of the barrel wall in stepwise increments.

4. The fiber-reinforced medical balloon of claim 1 wherein the fiber pitch in first and second longitudinally spaced apart portions of the barrel wall is greater than the fiber pitch in a third portion of the barrel wall separating the spaced apart portions.

5. The fiber-reinforced medical balloon of claim 1 wherein the fiber pitch in first and second longitudinally spaced apart portions of the barrel wall is less than the fiber pitch in a third portion of the barrel wall separating the first and second portions.

6. The fiber-reinforced medical balloon of claim 1 wherein the fiber pitch in first, second and third longitudinally spaced apart portions of the barrel wall is greater than the fiber pitch in longitudinally spaced apart fourth and fifth portions of the barrel wall separating the first, second and third longitudinally spaced apart portions of the barrel wall.

7. The fiber-reinforced medical balloon of claim 1 wherein the balloon is semi-compliant.

8. The fiber-reinforced medical balloon of claim 1 wherein the balloon is noncompliant.

9. The fiber-reinforced medical balloon of claim 1 wherein the fibers are substantially ribbon-shaped.

10. The fiber-reinforced medical balloon of claim 9 wherein the fibers have a width-to-thickness ratio in the range from about 25:1 to about 45:1.

11. The fiber-reinforced medical balloon of claim 9 wherein the fibers have a width-to-thickness ratio in the range from about 30:1 to about 40:1.

12. A medical balloon that may be inflated and deflated, the balloon comprising:
   a fiber layer comprised of ribbon-shaped fiber embedded in a continuous matrix of polymer material defining a generally cylindrical barrel wall in an inflated condition;
   wherein the fiber of the fiber layer extends around a longitudinal axis of the balloon in a series of circumferential fiber wraps over at least a portion of the barrel wall, wherein the distance between the fiber wraps defines a fiber pitch; and
   wherein the distance between adjacent fiber wraps varies over the barrel wall in non-linear increments.

13. The medical balloon of claim 12 wherein the distance between adjacent fiber wraps varies in step-wise increments.

14. The medical balloon of claim 12 wherein the fibers have a width-to-thickness ratio in the range from about 25:1 to about 45:1.

15. The medical balloon of claim 12 wherein the fibers have a width-to-thickness ratio in the range from about 30:1 to about 40:1.

16. The medical balloon of claim 12 wherein the fiber pitch in first and second longitudinally spaced apart portions of the barrel wall is greater than the fiber pitch in a third portion of the barrel wall separating the spaced apart portions.

17. The medical balloon of claim 12 wherein the fiber pitch in first and second longitudinally spaced apart portions of the barrel wall is less than the fiber pitch in a third portion of the barrel wall separating the first and second portions.

18. The medical balloon of claim 12 wherein the fiber pitch in first, second and third longitudinally spaced apart portions of the barrel wall is greater than the fiber pitch in longitudinally spaced apart fourth and fifth portions of the barrel wall separating the first, second and third longitudinally spaced apart portions of the barrel wall.

19. The medical balloon of claim 12, wherein the barrel wall includes proximal and distal ends disposed between tapered cone walls and proximal and distal cylindrical neck walls extending therefrom along the longitudinal axis of the balloon, and wherein the fiber layer extends continuously between the ends of the neck walls around the cone sections and barrel wall.

20. A fiber-reinforced medical balloon that may be inflated and deflated, the balloon comprising:
   a base balloon formed from a polymer material defining a generally cylindrical barrel wall in an inflated condition;
   a fiber layer extending around a longitudinal axis of the balloon in a series of circumferential fiber wraps over the length of the barrel wall wherein the distance between the fiber wraps defines a fiber pitch;
   an outer layer formed over the fiber layer, the outer layer comprising a polymer material in direct contact with the base balloon; and
   wherein the fiber pitch in a first portion of the barrel wall is less than the fiber pitch in a second portion of the barrel wall.

\* \* \* \* \*